(12) United States Patent
Kataoka et al.

(10) Patent No.: US 7,713,230 B2
(45) Date of Patent: May 11, 2010

(54) BREAST PUMP

(75) Inventors: Shinichi Kataoka, Tokyo (JP); Mitsuo Tashiro, Tokyo (JP)

(73) Assignee: Pigeon Corporation, Tokyo (JP)

( * ) Notice: Subject to any disclaimer, the term of this patent is extended or adjusted under 35 U.S.C. 154(b) by 0 days.

(21) Appl. No.: 12/022,986

(22) Filed: Jan. 30, 2008

(65) Prior Publication Data

US 2008/0195039 A1 Aug. 14, 2008

(30) Foreign Application Priority Data

Feb. 8, 2007 (JP) ............................. 2007-029350

(51) Int. Cl.
*A61M 1/06* (2006.01)
(52) U.S. Cl. ...................................... 604/74
(58) Field of Classification Search .................... 604/74
See application file for complete search history.

(56) References Cited

U.S. PATENT DOCUMENTS

| 6,749,582 | B2 * | 6/2004 | Britto et al. .................... 604/74 |
| 2005/0015045 | A1 * | 1/2005 | Tashiro et al. ................. 604/74 |
| 2005/0154348 | A1 * | 7/2005 | Lantz et al. .................... 604/74 |

FOREIGN PATENT DOCUMENTS

WO  WO 03013628 A1 *  2/2003

* cited by examiner

*Primary Examiner*—Nicholas D Lucchesi
*Assistant Examiner*—Jason Flick
(74) *Attorney, Agent, or Firm*—Cermak Kenealy Vaidya & Nakajima LLP

(57) ABSTRACT

A breast pump can be configured such that is can be easily dismantled for cleaning and easily re-assembled and is formed such that an operator or operating means thereof do not easily become detached during operation. The breast pump can include a storage container for storing milk, a breast pump main body, and an operator or operating means attached to the breast pump main body for deforming a negative pressure generating member attached to the breast pump main body. The operator can take the form of a lever, and can have an engaged portion that is engaged to an engagement portion on the breast pump main body side and includes an engagement opening formed on one end side of the operator. The engagement opening can include an insertion opening portion that is formed adjacent a bearing portion side and is larger than the outer form of the engagement portion, and a holding opening portion that is coextensive with the insertion opening portion but further toward the tip end side than the insertion opening portion. The holding opening can be smaller than the outer perimeter of the engagement portion.

18 Claims, 3 Drawing Sheets

// BREAST PUMP

This application claims the priority benefit under 35 U.S.C. §119 of Japanese Patent Application No. 2007-29350 filed on Feb. 8, 2007, which is hereby incorporated in its entirety by reference.

BACKGROUND

1. Technical Field

The presently disclosed subject matter relates to an improvement in a breast pump that is capable of milking and which uses manually or mechanically driven operator structures or means, for example.

2. Description of the Related Art

Breast pumps having a horn-shaped milking portion with an enlarged diameter that is brought into contact with the breast of a mother, or in other words an enlarged-diameter milking portion, are widely used.

In a well-known constitution for ensuring that the milk, which is formed into a mist by negative pressure generated during milking, does not leak out, a recess is provided in an upper end of a breast pump main body or the like and a deformable member such as a diaphragm is housed in the recess.

More specifically, in a well-known manual breast pump disclosed in U.S. Pat. No. 5,749,850, operating means such as a handle are connected to the diaphragm, and as a result of the reciprocating motion of the handle, the diaphragm is repeatedly pulled upward, thereby forming negative pressure.

Several other breast pumps having similar constitutions to the breast pump of U.S. Pat. No. 5,749,850 are known, for example, U.S. Pat. No. 6,749,582, WO2003/013628, WO2004/000390, and so on.

In another well-known breast pump (see U.S. Patent Publication No. 2004/039330), a recessed portion is provided on the handle side and a diaphragm is housed in the recessed portion. As a result, negative pressure is transmitted through an air passage extending from the breast pump main body side.

In a well-known breast pump described in U.S. Pat. No. 5,009,638, a cylinder is disposed in an upper portion of the breast pump main body, and a cup-shaped diaphragm is disposed and sealed in the cylinder. The diaphragm is deformed by negative pressure from a machine or the like, and as the diaphragm deforms, the internal pressure of the breast pump main body turns into negative pressure.

However, in these breast pumps, backflow milk and mist-form milk may infiltrate the recess or recessed portion housing the deforming portion such as the diaphragm.

Meanwhile, since a breast pump is used to extract milk to be fed to an infant or the like, it should be possible to clean the breast pump easily and thoroughly following milking when milk or the like infiltrates the recess or recessed portion so that the breast pump can be used hygienically.

In this case, the operating means for applying human or mechanical force to the diaphragm or other deforming portion, which take the form of a lever or the like, for example, can be structured such that they can be attached and detached easily during cleaning and prevented from becoming detached when attached.

SUMMARY

The presently disclosed subject matter has been designed to address the above and other problems and characteristics described above, and to provide a breast pump that can be dismantled for cleaning and assembled easily and is formed such that operating parts thereof do not easily become detached during operation.

According to a first aspect of the disclosed subject matter, a breast pump can have a storage container for storing milk, an attachment/detachment portion for attaching and detaching a breast pump main body to and from the storage container, and operating means or operator structure attached to the breast pump main body for deforming a negative pressure generating member attached to the breast pump main body. The breast pump main body can include an enlarged-diameter milking portion that increases in diameter toward a tip end that is brought into contact with a breast of a user; a small valve chamber that is disposed so as to face the storage container and communicates with the enlarged-diameter milking portion; and an attachment portion communicating with the small valve chamber, to which the negative pressure generating member, which generates a negative pressure for milking, is attached. The negative pressure generating member can include: a joint portion that is joined to the operating means by an engagement portion formed by enlarging the diameter of a tip end side of an extension portion that extends in rod form; an attachment/detachment portion that is molded from a comparatively flexible material possessing elasticity, and attached to and detached from the attachment portion of the breast pump main body; a wall portion that is provided integrally with the attachment/detachment portion and stands upright substantially vertically; and a deforming portion that is provided on the inside of the wall portion integrally with the wall portion, is thinner than the wall portion, and deforms upon reception of a force from the joint portion to thereby generate the negative pressure. The operating means or operator structure can include: a bearing portion that is supported rotatably on a spindle portion provided on the breast pump main body; an engaged portion that is disposed on one end side and joined to the joint portion; and a lever portion disposed on the other end side, the engaged portion comprises an engagement opening formed in the one end side of the operating means or structure. The engagement opening can include: an insertion opening portion that is formed on the bearing portion side and is larger than an outer form of the engagement portion; and a holding opening portion that is provided in contact with the insertion opening portion but further toward the tip end side than the insertion opening portion, and is smaller than the outer form of the engagement portion.

According to the first aspect of the disclosed subject matter, when the open tip end of the enlarged-diameter milking portion is brought into contact with the breast of the user and the operating means or structure are operated while the breast pump main body is attached to the storage container by the attachment/detachment portion, negative pressure is generated by the negative pressure generating member, and as a result, the milk that is aspirated from the breast of the user drips into the storage container through the small valve chamber and accumulates there.

In this case, the negative pressure generating member is disposed on, and attached to/detached from, the outside of the breast pump main body, and is attached to the attachment portion of the breast pump main body by the attachment/detachment portion. The deforming portion can deform as a result of a force that is applied by the operating means or structure via the joint portion, thereby generating negative pressure for aspirating the milk.

In the negative pressure generating member, the attachment/detachment portion that is attached to and detached from the attachment portion of the breast pump main body, the wall portion that stands upright substantially vertically, and the deforming portion can be formed integrally, and therefore, when the negative pressure generating member is detached from the breast pump main body, a hard recessed portion or recess formed by molding for accommodating a deforming portion such as a diaphragm does not exist on the main body side. Therefore, a situation in which milk residue and so on cling to a recess or the like resulting in residue or an accumulation that is difficult to wash, and making the breast pump unhygienic, does not arise. Further, since the entire or substantially entire negative pressure generating member can be formed from a flexible material possessing elasticity, the user can detach the negative pressure generating member from the breast pump main body for washing by deforming the negative pressure generating member using manual force, and the negative pressure generating member can be washed thoroughly with ease.

Further, the engagement opening of the operating means or structure can include the insertion opening portion, which is formed on the bearing portion side and is larger than the outer form of the engagement portion, and the holding opening portion, which is provided in contact with the insertion opening portion but further toward the tip end side than the insertion opening portion, and is smaller than the outer form of the engagement portion.

Hence, when the boss-shaped engagement portion is inserted through the insertion opening portion such that the bearing portion is supported rotatably on the spindle portion, for example, the joint portion moves into the holding opening portion contacting the insertion opening portion through a single touch. When the operating means or structure are operated such that the rod-shaped extension portion of the negative pressure generating member reciprocates vertically, the joint portion remains positioned in the holding opening portion even when the rod-shaped extension portion is in an elevated position. The holding opening portion is smaller than the outer form of the engagement portion, and therefore the joint portion does not become detached from the holding opening portion.

It is therefore possible to realize a structure whereby the operating means or structure are attached and detached easily using the insertion opening portion when dismantling the breast pump for washing or the like, and the operating means or structure does not easily become detached during operation.

In accordance with a second aspect of the disclosed subject matter, the insertion opening portion and the holding opening portion of the engagement opening can form an integrated elongated hole such that the engagement portion reciprocates within the elongated hole in accordance with the vertically reciprocating displacement of the rod-shaped extension portion of the negative pressure generating member.

According to the second aspect of the disclosed subject matter, the extension portion slides within the elongated hole, and therefore the force required to generate negative pressure can be applied without hindering the vertical reciprocation of the extension portion.

In accordance with a third aspect of the disclosed subject matter, when the lever portion is disposed on an imaginary horizontal plane such that the inside of the elongated operating means or structure faces downward, a peripheral edge portion of the engagement opening is formed at an incline such that the insertion opening portion of the engagement opening is set in a higher position than the holding opening portion.

According to the third aspect of the disclosed subject matter, the engagement opening is formed as an inclined hole, and therefore the joint portion can be inserted into the insertion opening portion and moved to the holding opening portion on the tip end side easily, leading to an improvement in the workability of the attachment operation.

In accordance with a fourth aspect of the disclosed subject matter, a slippage prevention portion can be formed integrally with at least a part of an outer surface of the lever portion.

According to the fourth aspect of the disclosed subject matter, when a manual operating means or structure is employed, slippage is unlikely to occur during operation, leading to an improvement in user-friendliness.

In accordance with a fifth aspect of the disclosed subject matter, the wall portion provided integrally with the attachment/detachment portion so as to stand upright substantially vertically can possess enough rigidity to maintain the outer form of the upright wall portion when the rod-shaped extension portion of the negative pressure generating member reciprocates vertically.

According to the fifth aspect of the disclosed subject matter, the attachment/detachment portion of the negative pressure generating member is formed integrally with the wall portion possessing enough rigidity to maintain the outer form of the upright wall portion, and therefore attachment/detachment operations are performed easily by holding the wall portion.

DETAILED DESCRIPTION OF EXEMPLARY EMBODIMENTS

Exemplary embodiments of the presently disclosed subject matter will be described in detail below with reference to the attached drawings.

Note that the embodiments to be described below are specific examples of the presently disclosed subject matter, and therefore include various technical features and characteristics. However, it should be understood that the scope of the presently disclosed subject matter is not limited to these embodiments.

Figure 1:
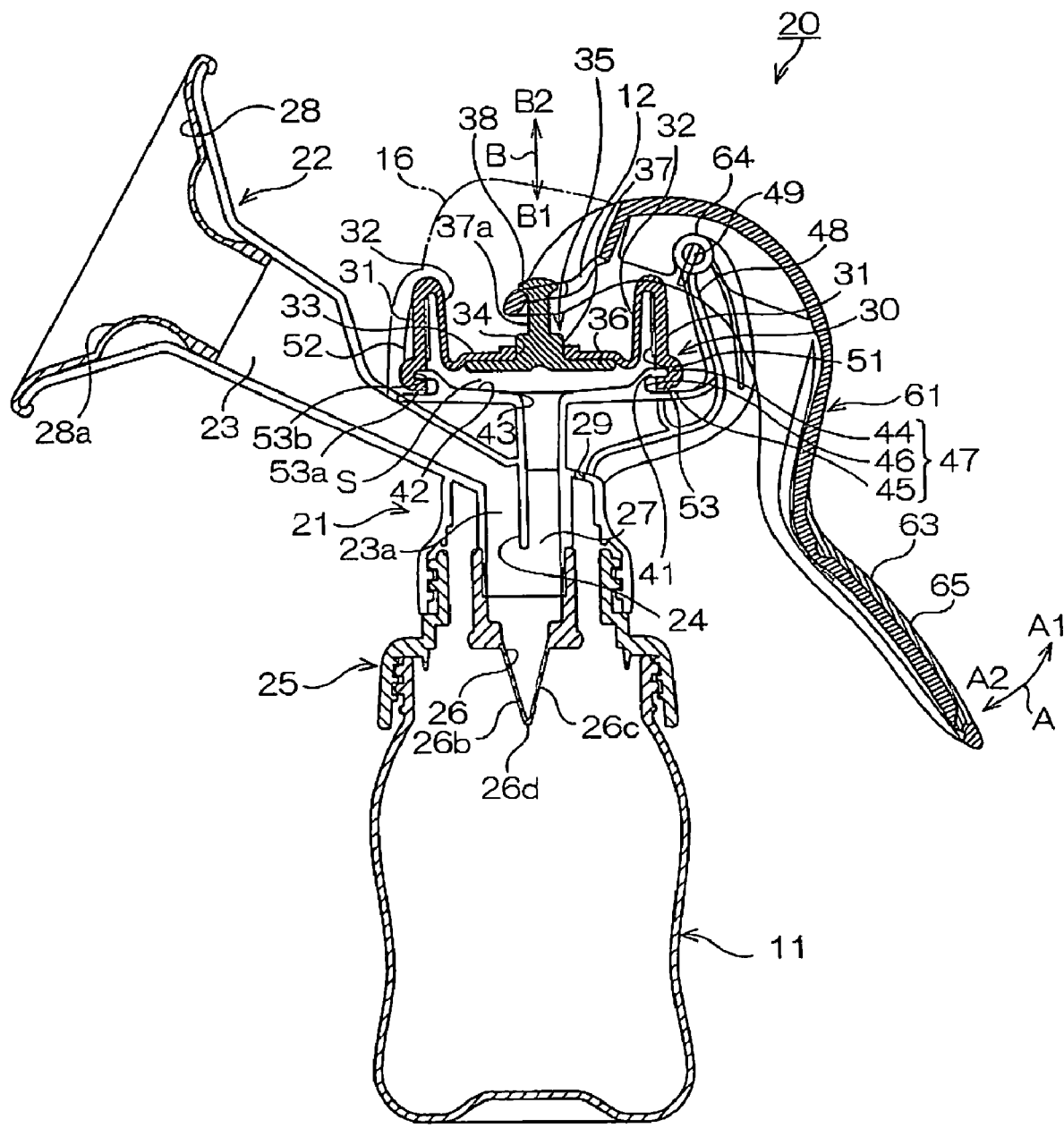
FIG. 1 is a schematic sectional view of an example of a breast pump made in accordance with principles of the disclosed subject matter.
Figure 2:
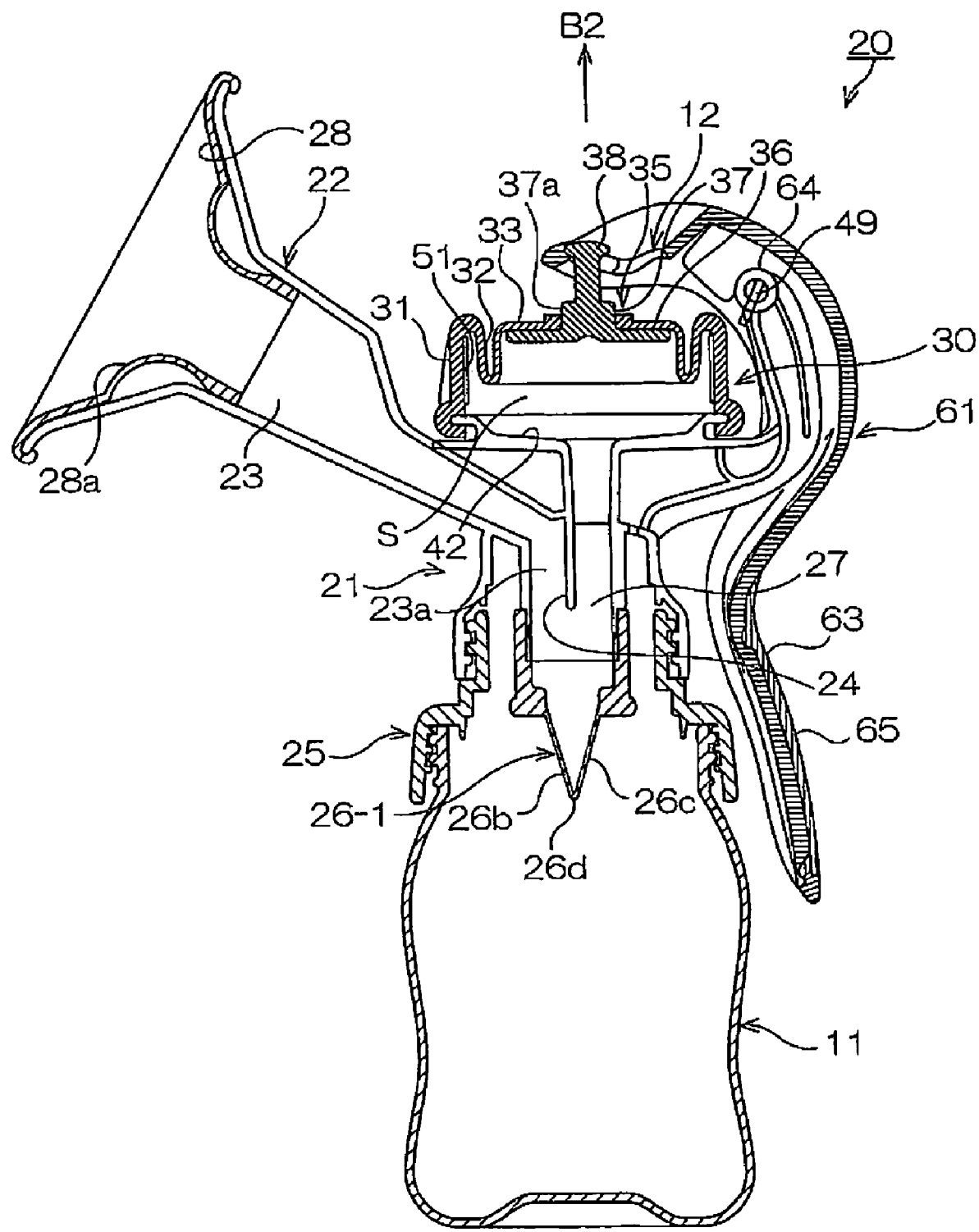
FIG. 2 is another schematic sectional view of a breast pump according to an embodiment of the presently disclosed subject matter.

FIGS. 1 and 2 are schematic sectional views showing an example of a breast pump according to an embodiment of the presently disclosed subject matter.

A breast pump 20 can include a breast pump main body 21 (to be referred to as the "main body" hereafter), a handle 61 serving as operating means, and a bottle 11 serving as a storage container for storing expressed milk. The handle 61 can be attached to and detached from the breast pump main body 21.

Further, as shown in FIG. 1, a substantially dome-shaped hood 16 is detachably attached to an upper portion of the main body 21 to which a negative pressure generating member 30 is attached.

The hood 16 is cut away in the location of the handle 61, and when the hood 16 is attached avoiding the handle 61, it is capable of covering and protecting the negative pressure generating member 30 and so on. Note that the hood 16 need not be used.

The entire main body 21 can be molded using a comparatively lightweight, strong synthetic resin material such as polypropylene, polycarbonate, polycycloolefin, polyethersulphone, or polyphenylsulphone, for example.

The main body 21 can include an adaptor 25 for attaching and detaching the main body 21 to and from the bottle 11. As shown in FIG. 1, for example, the adaptor 25 is a flattened tubular body having a small diameter in an upper portion and a large diameter in a lower portion.

A male screw portion is formed on the upper portion outer periphery of the adaptor 25, and this male screw portion is screwed to a female screw portion formed in the lower portion of the main body 21, or in other words forms an attachment/detachment portion. A female screw portion is formed in a lower portion of the adaptor 25, and this female screw portion is screwed to a male screw portion formed on the upper end outer periphery of the bottle 11.

Note that the bottle 11 may be a dedicated component of the breast pump 20, or a feeding bottle or the like that fits the adaptor 25. Further, the bottle 11 may take the form of a bag rather than a molded container.

A conical or horn-shaped enlarged-diameter milking portion 22, the tip end of which has an enlarged diameter, is provided on an upper portion of the adaptor 25 of the main body 21 in a diagonally inclined state. A buffering portion 28 constituted by an elastic body made of silicone rubber, elastomer, natural rubber, or similar can be detachably attached to an opening side of the enlarged-diameter milking portion 22. The buffering portion 28 reduces stimulation that may occur when the enlarged-diameter milking portion 22 is brought into contact with the breast during milking, thereby ensuring that no pain is felt by the user. Projecting portions 28a can be provided for applying stimulation to the vicinity of the areolae of the user and are formed in a plurality of locations, for example upper and lower locations, on the inner peripheral surface of the buffering portion 28.

A milking portion air passage 23 of the enlarged-diameter milking portion 22 serves as a passage for air and expressed milk, which bends downward and extends to the bottle 11 side. Further, an opening of the milking portion air passage 23 in the enlarged-diameter milking portion 22 is located inside the adaptor 25 for attaching the main body 21 to the bottle 11, and a small valve chamber 26 is attached thereto. A further air passage 27 is provided adjacent to a downwardly oriented part 23a of the milking portion air passage 23 via a partition wall 24. As shown in the drawings, a lower end opening of the air passage 27 communicates with the downwardly oriented part 23a of the milking portion air passage within the small valve chamber 26.

An upper end of the air passage 27 forms an opening 43, and an attachment portion 41 that widens into a substantially circular shape is provided so as to surround the opening 43. The attachment portion 41 serves as a part for attaching the negative pressure generating member 30. The negative pressure generating member 30 will be described in further detail below.

An upper surface of the attachment portion 41 is formed as an inclined surface 42 that inclines slightly downward toward the opening 43.

The small valve chamber 26 is a hollow cap-shaped member that can be constituted in its entirety by an elastic body made of silicone rubber, elastomer, natural rubber, or similar material. Two side walls 26b, 26c on a lower end side thereof can be thinly formed, and together constitute a valve body made of elastic inclined walls that approach each other gradually toward the lower end, thereby reducing the width of the valve body. A slit 26d is provided in the lower end where the two side walls 26b, 26c approach each other, and when the expressed milk accumulates to a predetermined amount in the hollow interior of the small valve chamber 26, the slit 26d opens under the weight of the milk and in accordance with pressure variation occurring when negative pressure is released, as will be described below, whereby the milk drips into the bottle 11. Further, by forming the slit 26d in the lower end of the inclined walls, air in the bottle 11 can be prevented from entering the small chamber 26 during periods of negative pressure.

Furthermore, a small air hole 29 that connects the interior of the bottle 11 to the outside air is formed in a location of the breast pump main body 21 adjacent to the adaptor 25 so that pressure generated as the milk accumulates in the bottle 11 can escape.

The negative pressure generating member 30 takes an overall form approaching a comparatively flat, closed-end cylindrical body.

More specifically, the negative pressure generating member 30 can include a first wall portion 31 that stands upright on the outside of the negative pressure generating member 30 and is sufficiently rigid to maintain the outer diameter thereof, and a second wall portion 32 serving as an inside wall portion, which is integrated with the first wall portion 31, folded back toward the inside from an upper end portion, and formed to be thin from the part that extends from the folded back location. The second wall portion 32 serves as a deforming portion, and a lower end thereof forms a bottom surface portion 33, or more specifically a comparatively wide inside bottom portion provided as an integral extension that blocks the cylindrical lower portion of the negative pressure generating member 30.

The first wall portion 31 and second wall portion 32 can be formed from the same material, but by varying the thickness of the material, the rigidity of the first wall portion 31 and second wall portion 32 can be made different. Hence, the first wall portion 31 can be formed so as not to deform, whereas the second wall portion 32 can be formed with the capability of deforming and being disposed in alignment with the first wall portion 31 such that a constant amount of negative pressure is secured, as will be described below.

In other words, the negative pressure generating member 30 can be formed such that when the handle 61 is operated in a manner to be described below, the second wall portion 32, i.e. the deforming portion, deforms so as to modify the volume of an internal space S formed between the bottom surface portion 33 and the attachment portion 41, and as a result, air in the milking portion air passage 23, which communicates with the internal space S via the air passage 27 and the small valve chamber 26, is aspirated such that negative pressure can be formed.

At this time, the wall portion, i.e. the first wall portion 31, exhibits substantially no deformation, and therefore the state of attachment to the attachment portion 41 can be maintained.

A reinforcement rib 52 extending in a longitudinal direction can be formed on the outer surface of the first wall portion 31 to reinforce the wall shape maintaining function.

Further, a projecting portion 51 extending in the longitudinal direction can be provided on the surface of the first wall portion 31 that opposes the second wall portion 32, i.e. the deforming portion, so as to be interposed between the first and second wall portions 31, 32. Here, the projecting portion 51 is formed on the inner surface side of the first wall portion 31.

When the second wall portion 32, i.e. the deforming portion, returns to its original shape during repeated deformation and restoration, the projecting portion 51 serves as a spacer interposed on the surface of the first wall portion 31 opposing the second wall portion 32, and therefore an operating noise generated when the first and second wall portions 31, 32 abut against each other is effectively prevented from becoming unpleasant.

A joint portion (member) 35 can be provided for deforming the second wall portion 32 serving as the deforming portion.

The joint portion (member) 35 is formed from a hard material different to the material of the second wall portion 32, i.e. the deforming portion. The entire joint portion (member) 35 can be formed from a comparatively hard synthetic resin such as polypropylene, polycarbonate, polycycloolefin, or polyethersulphone, for example. The joint portion (member) 35 can include a flat disc-shaped base portion 36, the base end portion of which has a widely enlarged diameter. The joint portion (member) 35 can also be disposed such that a bottom surface of the base portion 36 is positioned above the internal space S on the main body 21 side. The joint portion (member) 35 can also include a boss portion 37 that is formed integrally with and on top of the base portion 36, stands upright to a low height, and has a large enough outer diameter to provide the joint portion (member) 35 with strength, and an extension portion 37a that extends in the form of a comparatively narrow rod from the boss portion 37. Furthermore, a circular, elliptical or oval engagement portion 38 can be provided as a bulging portion or an enlarged-diameter portion on the tip end of the extension portion 37a.

A penetrating hole or a through hole 34 can be formed in a central portion of the bottom surface portion 33.

More specifically, when the negative pressure generating member 30 and the joint member 35 are formed separately, the reference numeral 34 denotes a through hole. The through hole 34 has a slightly smaller inner diameter than the outer diameter of the boss portion 37 such that when the boss portion 37 is inserted into the through hole 34 from a rear surface of the bottom surface portion 33, the negative pressure generating member 30 and joint member 35 can be attached easily while maintaining a tight seal therebetween. In this case, attachment and detachment for cleaning and so on can be easily performed.

On the other hand, the joint portion 35 may be integrally joined to the bottom surface portion 33 and the penetrating hole 34 by two-color molding or insert molding. In this case, a corresponding increase in manufacturing costs may occur, but since the entire negative pressure generating member 30 becomes an integrated component, handling thereof is easy.

The negative pressure generating member 30 described above can be attached to and detached from a substantially circular peripheral edge portion 47 of the attachment portion 41 of the breast pump main body 21 by a substantially circular attachment/detachment portion 53, the peripheral edge portion 47 having a slightly smaller diameter than the attachment/detachment portion 53.

The attachment/detachment portion 53 of the negative pressure generating member 30 can include an inwardly oriented flange 53a that serves as a negative pressure generation side flange portion and is formed as a downward extension of the first wall portion 31 which curves inward so as to project inwardly at its lower end, and an inner groove 53b that serves as a negative pressure generation side groove portion and is formed on the upper side and inside of the inwardly oriented flange 53a. The entire attachment/detachment portion 53 possesses predetermined rubber elasticity.

Meanwhile, an outwardly oriented, two-layer flange is formed on the peripheral edge portion 47 of the attachment portion 41. More specifically, the attachment portion 41 comprises a first flange 44 formed on the upper end of the attachment portion 41 as an outwardly projecting main body side flange portion, and a second flange 45 formed below the first flange 44 as positioning means having a larger outer diameter than the lower end of the attachment/detachment portion 53 and the first flange 44. Furthermore, an outer groove 46 is formed as an inwardly intruding main body side groove portion by the reduced diameter between the first flange 44 and second flange 45.

Hence, the user grips the wall surface constituted by the first wall portion 31 and second wall portion 32 of the negative pressure generating member 30 and brings the outer surface of the inwardly oriented flange 53a, i.e. the lower end of the attachment/detachment portion 53, on the opposite side of the gripping position into contact with the upwardly oriented step portion of the second flange 45 serving as the positioning means. Then, with the inwardly oriented flange 53a latched to the outer groove 46, the user pulls the negative pressure generating member 30 with the gripping hand while lightly restraining the latched position with a finger of the non-gripping hand. In so doing, the inwardly oriented flange 53a, excluding the latched position, deforms so as to get over the first flange 44 and enter the main body side groove portion 46. Thus, the entire attachment/detachment portion 53 is attached to the peripheral edge portion 47 such that the first flange 44 enters the inner groove 53b and the inwardly oriented flange 53a enters the outer groove 46, and as a result, a tightly sealed attachment is formed.

In this manner, the negative pressure generating member 30 is attached extremely easily. More specifically, the second flange 45 is formed in a position that is slightly further removed from the first flange 44 than the thickness of the inwardly oriented flange 53a, and therefore forms a projecting rib that prevents the inwardly oriented flange 53a from getting over the outer groove 46 during attachment.

Conversely, when detaching the negative pressure generating member 30, the inwardly oriented flange 53a can be dislodged from the outer groove 46 and caused to get over the first flange 44 by simply holding the first wall portion 31 by hand and expanding the first wall portion 31 outward. Thus, the negative pressure generating member 30 can be detached extremely easily.

Note that in this embodiment, the second flange 45 has a similar shape to the first flange 44, but as long as a part thereof projects further than the first flange 44, a notch may be formed in the side edge side so that it can be restrained more easily by the fingers, for example.

Here, the first wall portion 31, second wall portion 32, and bottom surface portion 33 of the negative pressure generating member 30 can be formed integrally from a flexible material having comparatively high overall elasticity, more specifically a synthetic resin having a hardness between HS30 and 70 according to the A-type durometer of JIS-K6253 (ISO7619), such as silicone rubber, isoprene rubber, or an elastomer such as SEBS (styrene-ethylene-butylene-styrene), for example.

Further, the thickness of the material constituting the first wall portion 31 part can be set between 1.5 mm and 3.0 mm, while the thickness of the material constituting the second wall portion 32 can be set between 1.0 mm and 2.5 mm.

When the hardness of the negative pressure generating member 30 is lower than HS30, the first wall portion 31 may deform and the amount of generated negative pressure may decrease. When the hardness exceeds HS60, the force required to operate the handle 61 to be described below increases, making the negative pressure formation operation more difficult.

When the thickness of the second wall portion 32 is smaller than 1.0 mm, elongating deformation may be produced by the rubber elasticity during deformation increases, leading to a reduction in the amount of generated negative pressure. When the thickness exceeds 2.5 mm, the force required to operate the handle 61 serving as the operating means to be described below increases, making the negative pressure formation operation more difficult.

When the thickness of the first wall portion 31 is smaller than 1.5 mm, the wall portion may buckle during negative pressure formation. In other words, unnecessary deformation may occur, making it difficult or impossible to generate sufficient negative pressure. When the thickness of the first wall portion 31 exceeds 3.0 mm, the wall portion may not deform sufficiently during attachment to the breast pump main body 21, making the attachment operation more difficult.

In the upper portion of the main body 21, an arm 48 for attaching the handle 61 extends from an opposite position to the position in which the milking portion 22 extends. The tip end of the arm 48 is positioned adjacent to the negative pressure generating member 30 in a location above the upper end of the negative pressure generating member 30. In this embodiment, a horizontally disposed, cylindrical spindle portion 49 is provided on the tip end of the arm 48. Note that an arm rib can be formed substantially along the center of the arm 48 to increase the strength of the arm 48 so that the arm 48 does not break if it is dropped or the like.

In this embodiment, the handle 61 is shown as an example of manual operating means, and is a component with an overall elongated form, for example. More specifically, the handle 61 can be a molded component formed integrally from a comparatively sturdy, lightweight synthetic resin such as polypropylene, polycarbonate, polycycloolefin, or polyethersulphone, for example.

As shown in FIG. 1, the handle 61 can be attached to and detached from the engagement portion 38 of the joint portion (member) 35 easily. The other end of the handle 61 takes a low position and juts outward slightly, thereby forming a lever portion 63 having a lever-shaped appearance, which is gripped in a manner to be described below.

More specifically, the handle 61 is attached and detached to and from the main body 21, and in the fixed state shown in FIG. 1, the handle 61 is attached so as to be capable of rotating relative to the spindle portion 49 on the tip end of the arm 48 of the main body 21 by means of a bearing portion 64 provided in a position approaching one end of the handle 61.

A slippage prevention portion 65 is provided on the outside of the other end of the handle 61. Hence, as shown by arrow A in FIG. 1, when an operator operates the lever portion 63 with the hand, the handle 61 performs a reciprocating motion toward/away from the bottle 11. Note that the slippage prevention portion 65 may be formed by applying elastomer through two-color molding or the like, and processing to increase frictional force may be implemented on the surface of the corresponding location of the handle 61 by providing irregularities such as texture or ribs to reduce the likelihood of slippage.

In accordance with the reciprocating motion of the handle 61, an engaged portion 12 positioned on one end of the handle 61 performs a vertical reciprocating motion by rotating about the spindle portion 49, as shown by an arrow B.

As shown in FIG. 2, when the user moves the lever portion 63 in the direction A2, or in other words so as to approach the bottle 11, such that the engaged portion 12 moves in the direction of an arrow B2, the second wall portion 32 serving as the deforming portion of the negative pressure generating member 30 is deformed upward from its downwardly oriented state in FIG. 1.

When the volume of the internal space S formed between the bottom surface portion 33 and the inclined surface 42 increases as a result, the air in the milking portion air passage 23 is extracted in an amount corresponding to the air that is drawn into the internal space S, and when the breast of the user is brought into contact with the enlarged-diameter tip end of the milking portion 22, a tightly sealed space is formed, causing the pressure in the milking portion air passage 23 to turn negative.

As a result of this negative pressure, expressed milk enters the small valve chamber 26 from the downwardly oriented part 23a of the milking portion air passage, and thus a certain amount of milk accumulates in the small valve chamber 26. Since the two side walls 26b, 26c are formed thinly, the negative pressure causes them to deform slightly in an approaching direction at this time, ensuring that the slit 26d remains tightly closed, and therefore the milk does not leak out.

As shown in FIG. 2, when the user operates the handle 61 to a position closest to the bottle 11, the engaged portion 12 reaches an uppermost movement position, whereby the inside tip end of the handle 61 comes into contact with the outer edge of the bottle 11 and stops moving. In this state, the second wall portion 32 serving as the deforming portion stops in an intermediately lifted state and attempts to return to its original shape toward the lower side, i.e. in the B1 direction shown in FIG. 1.

Hence, when the user reduces the force applied to the handle 61, the engaged portion 12 is moved in the direction of the arrow B1 by the restoration force of the second wall portion 32, and the handle 61 moves in a direction away from the bottle 11 such that the second wall portion 32 serving as the deforming portion of the negative pressure generating member 30 returns to the state shown in FIG. 1. During this process, the volume of the internal space S formed between the bottom surface portion 33 and the inclined surface 42 decreases, and as a result of pressure variation occurring when the negative pressure is released and the weight of the accumulated milk, the tip end sides of the two side walls 26b, 26c open, causing the slit 26d to open such that the milk drips into the bottle 11.

By repeating the operation described above, negative pressure is applied in pulse form on the basis of the operation of the negative pressure generating member 30 and in accordance with the operation of the handle 61, and thus milking is performed.

To ensure that the engagement portion 38 does not become detached from the engaged portion 12 of the handle 61 when the handle 61 serving as the operating means is biased in the A1 direction by the restoration force of the negative pressure generating member 30 during this operation, the following constitution can be provided.

Figure 3:
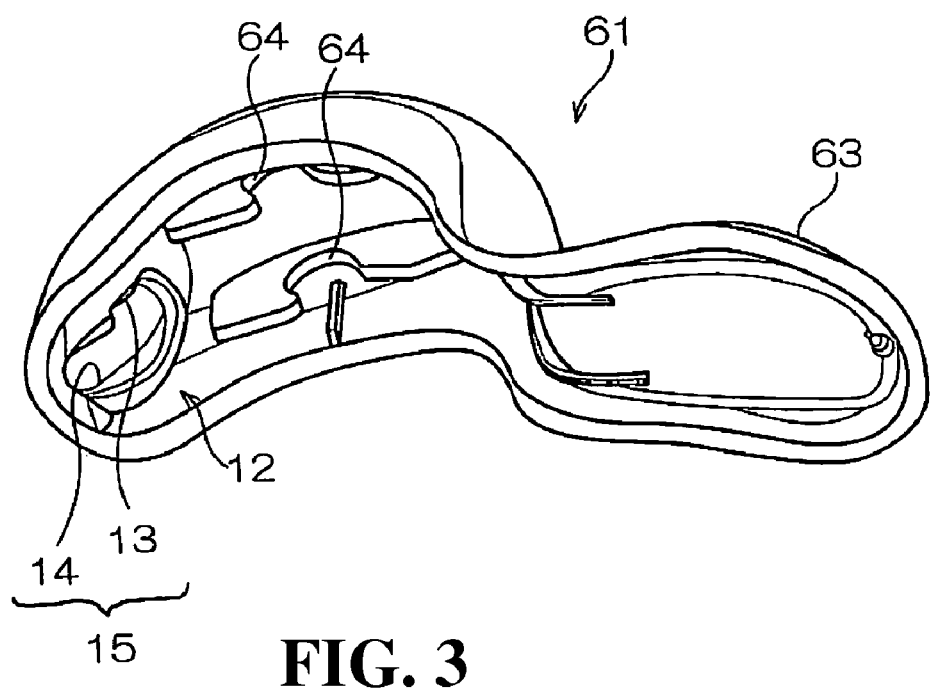
FIG. 3 is a schematic perspective view showing the operating means or handle of the breast pump shown in FIG. 1.

FIG. 3 is a schematic perspective view showing the inside of the handle 61 from below, assuming that the handle 61 is disposed on an imaginary horizontal plane facing downward.

As shown in FIG. 3, the engaged portion 12 is provided near the tip end of the handle 61. The engaged portion 12 includes an engagement opening 15 formed in a tip end side on one end of the handle portion 61. The engagement opening 15 can include at least an insertion opening portion 13 formed on the bearing portion 64 side when the handle 61 is attached to the breast pump 20 as shown in FIG. 1, which is larger than the outer form of the engagement portion 38, and a holding opening portion 14 provided in contact with the insertion opening portion 13 but closer to the tip end side, which is smaller than the outer form of the engagement portion 38.

Figure 4:
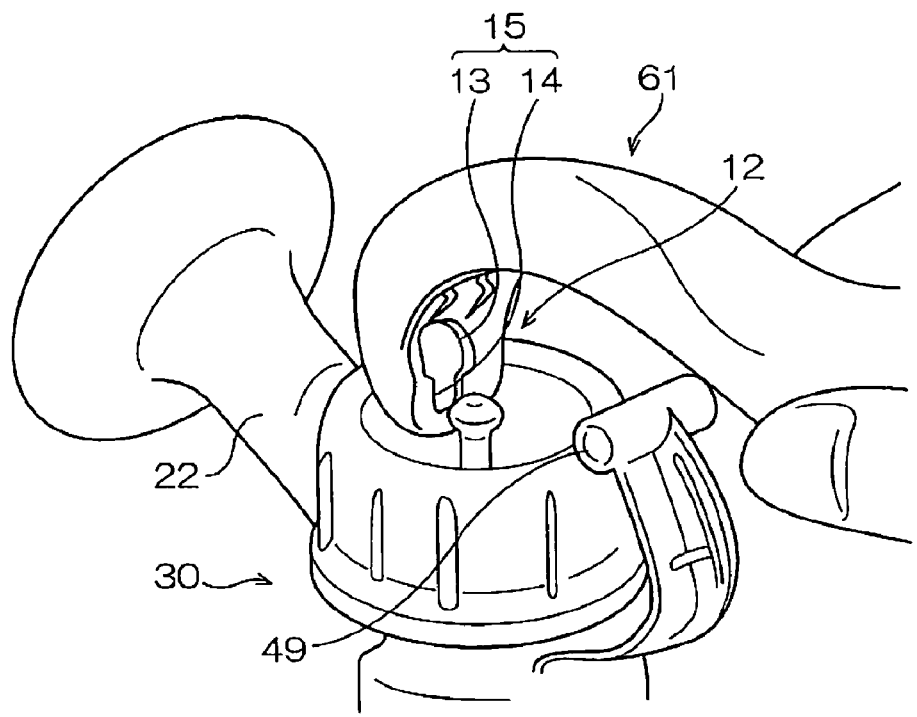
FIG. 4 is an illustrative view showing a state in which an engagement portion is engaged to an engagement opening of the handle shown in FIG. 3.

Hence, as shown in FIG. 4, when the boss-shaped engagement portion 38 of this embodiment is inserted through the insertion opening portion 13 having a large opening diameter such that the bearing portion 64 is supported rotatably on the spindle portion 49, for example, the joint portion 35 moves into the holding opening portion 14 from the insertion opening portion 13. When the handle 61 is operated such that the rod-shaped extension portion 37a (see FIG. 1) of the negative pressure generating member 30 reciprocates vertically, the joint portion 35 remains positioned in the holding opening portion 14 located adjacent the insertion opening portion 13 even when the rod-shaped extension portion 37a is in an elevated position. The holding opening portion 14 is smaller than the outer form of the engagement portion 38, and therefore the joint portion 35 is held in the holding opening portion 14 by the engagement portion 38 and without becoming detached.

As shown in FIG. 3, the insertion opening portion 13 and holding opening portion 14 of the engagement opening 15 can be formed as an integrated elongated hole such that the engagement portion 38 reciprocates forward and back within the elongated hole in accordance with the vertically reciprocating displacement of the rod-shaped extension portion 37a of the negative pressure generating member 30.

When the extension portion 37a and the engagement portion 38 slides within the elongated hole in this manner, the force required to generate negative pressure can be applied without hindering the vertical reciprocation of the extension portion 37a.

Further, as shown in FIGS. 3 and 4, a peripheral edge portion of the elongated hole in the engagement opening 15 can be formed as an incline surface such that the insertion opening portion 13 is set in a higher position than the holding opening portion 14.

As a result, the elongated hole connecting the two openings forms an inclined hole, and therefore the engagement portion 38 can be inserted into the insertion opening portion 13 and moved to the holding opening portion 14 on the tip end side easily, leading to an improvement in the workability of the attachment operation.

According to the breast pump 20 of the embodiment described above, as is evident from the above description, the negative pressure generating member 30, which plays an important role in milking, comprises the attachment/detachment portion 53 that is attached to and detached from the attachment portion 41 of the breast pump main body 21, the first wall portion 31 having enough rigidity to maintain the outer form of the negative pressure generating member 30, and the second wall portion 32 serving as the deforming portion. All of these components can be formed integrally from an elastic resin.

Hence, when the negative pressure generating member 30 is detached from the breast pump main body 21, a recessed portion or a recess, which is formed by molding to accommodate a deforming portion such as a diaphragm, does not exist on the main body 21 side.

Therefore, a situation in which milk residue, etc., which clings to a recess or the like and which is difficult to wash, making the breast pump unhygienic, does not arise. Further, since the entire negative pressure generating member 30 is formed from a flexible material possessing elasticity, the user can easily detach the negative pressure generating member 30 from the breast pump main body 21 for washing by placing a finger near the attachment/detachment portion 53 and deforming the attachment/detachment portion 53 lightly toward the outside. Since the detached negative pressure generating member 30 can be formed entirely from a flexible material, it can be washed thoroughly with ease.

The present disclosed subject matter is not limited to the embodiments described above.

For example, the operating means or structure may be electric rather than manual.

The attachment portion 41 is formed in a horizontal direction so as to face upward, but may be disposed at a diagonally incline along the air passage 23. In this case, the air passage 27 on the negative pressure generating member 30 side can be formed in a position approaching one side of the attachment portion 41 so that the milk flows downward.

Further, not all of the individual constitutions of the embodiments described above are necessary, and a portion thereof may be omitted. In this case, the presently disclosed subject matter may be implemented by combining the individual constitutions with other constitutions not shown in the drawings to form different constitutions, and the constitutions of the various embodiments may also be combined for use.

While the subject matter has been described in detail with reference to exemplary embodiments thereof, it will be apparent to one skilled in the art that various changes can be made, and equivalents employed, without departing from the scope of the invention. The disclosure and teachings of all related and conventional art documents referenced above, including the various U.S. patents, are hereby incorporated by reference in their entirety.

What is claimed is:

1. A breast pump, comprising:
   a breast pump main body including a negative pressure generating member;
   a storage container configured to store milk, the container including an attachment/detachment portion configured to attach and detach the storage container to and from the breast pump main body; and
   an operator located adjacent the breast pump main body and configured to deform the negative pressure generating member of the breast pump main body,
   wherein the breast pump main body includes,
      an enlarged-diameter milking portion that increases in diameter toward a tip end configured to contact with a breast of a user,
      a small valve chamber configured to face the storage container and is in fluid communication with the enlarged-diameter milking portion, and
      an attachment portion in fluid communication with the small valve chamber and configured for attachment to the negative pressure generating member,
   the negative pressure generating member includes,
      a joint portion configured to be selectively joined to the operator by an engagement portion, the engagement portion formed by an enlarged diameter of a tip end side of an extension portion extending in rod form,
      an attachment/detachment portion molded from a comparatively flexible material and possessing elasticity, and the attachment/detachment portion configured to be attached to and detached from the attachment portion of the breast pump main body,
      a wall portion integrally formed with the attachment/detachment portion, and
      a deforming portion located on an inside of the wall portion, the deforming portion being thinner than the wall portion, and configured to deform upon reception of a force from the joint portion to thereby generate the negative pressure,
   the operator includes,
      a bearing portion rotatably supported on a spindle portion on the breast pump main body, an engaged portion that is disposed on one end of the operator and configured to be selectively joined to the joint portion, and a lever portion disposed an other end of the operator, the engaged portion includes an engagement opening located in the one end of the operator, and the engagement opening includes, an insertion opening portion located adjacent the bearing portion and being larger than an outer perimeter of the engagement portion, and a holding opening portion extending from the insertion opening portion and located closer to the tip end side of the joint portion than the insertion opening portion when the operator is operated, and is smaller than the outer perimeter of the engagement portion, and wherein the insertion opening portion is located between the holding opening portion and the lever portion.

2. The breast pump according to claim 1, wherein the insertion opening portion and the holding opening portion of the engagement opening form an integrated elongated hole such that the engagement portion reciprocates within the elongated hole in accordance with a vertically reciprocating displacement of the extension portion of the negative pressure generating member.

3. The breast pump according to claim 1, wherein, when the lever portion is disposed on an imaginary horizontal plane such that an inside of the elongated operator faces downward, a peripheral edge portion of the engagement opening is inclined such that the insertion opening portion is located in a vertically higher position than the holding opening portion.

4. The breast pump according to claim 2, wherein, when the lever portion is disposed on an imaginary horizontal plane such that the inside of the elongated operator faces downward, a peripheral edge portion of the engagement opening is inclined such that the insertion opening portion is located in a vertically higher position than the holding opening portion.

5. The breast pump according to claim 1, wherein a slippage prevention portion is formed integrally with at least a part of an outer surface of the lever portion.

6. The breast pump according to claim 2, wherein a slippage prevention portion is formed integrally with at least a part of an outer surface of the lever portion.

7. The breast pump according to claim 3, wherein a slippage prevention portion is formed integrally with at least a part of an outer surface of the lever portion.

8. The breast pump according to claim 1, wherein the wall portion integral with the attachment/detachment portion possesses enough rigidity to maintain an outer form of the wall portion in an upright configuration when the extension portion of the negative pressure generating member reciprocates vertically.

9. The breast pump according to claim 2, wherein the wall portion integral with the attachment/detachment portion possesses enough rigidity to maintain an outer form of the wall portion in an upright configuration when the extension portion of the negative pressure generating member reciprocates vertically.

10. The breast pump according to claim 3, wherein the wall portion integral with the attachment/detachment portion possesses enough rigidity to maintain an outer form of the wall portion in an upright configuration when the extension portion of the negative pressure generating member reciprocates vertically.

11. The breast pump according to claim 4, wherein the wall portion integral with the attachment/detachment portion possesses enough rigidity to maintain an outer form of the wall portion in an upright configuration when the extension portion of the negative pressure generating member reciprocates vertically.

12. The breast pump according to claim 1, wherein the operator includes means for deforming the negative pressure generating member and creating a reciprocating negative pressure within the main body.

13. The breast pump according to claim 1, wherein the insertion opening portion is located substantially within a first plane and the holding opening portion is located substantially within a second plane, and the first plane is angled with respect to the second plane.

14. The breast pump according to claim 1, wherein the operator is rotatably attached to the main body.

15. A breast pump, comprising:

a breast pump main body including a breast contact portion and a chamber, the breast contact portion being in fluid communication with the chamber;

a negative pressure generating member located adjacent the main body and having an engagement portion;

a storage container configured for attachment to the main body;

a valve located between the main body and the storage container; and an operator structure located adjacent the breast pump main body and rotatable with respect to the main body, the operator structure having a longitudinal axis and being connected to the engagement portion of the negative pressure generating member such that when the operator structure is rotated with respect to the main body the negative pressure generating member moves to cause a negative pressure in the chamber of the main body, the operator structure includes a lever portion disposed on one end of the operator structure, an engagement opening that has an insertion opening portion, and a holding opening portion spaced along the longitudinal axis of the operator structure, the engagement opening having a width that diminishes from the insertion opening portion to the holding opening portion along the longitudinal axis of the operator structure, and at least a portion of the insertion opening portion being located within a first plane and at least a portion of the holding opening portion being located within a second plane, and the first plane is angled with respect to the second plane, wherein a total distance between the insertion opening portion and the lever portion is less than a total distance between the holding opening portion and the lever portion.

16. The breast pump according to claim 15, wherein the operator structure is configured such that the engagement portion reciprocates within the engagement opening in accordance with a vertically reciprocating displacement of the engagement portion of the negative pressure generating member.

17. The breast pump according to claim 15, wherein, when the operator structure is disposed on an imaginary horizontal plane such that an inside of the operator structure faces downward, a peripheral edge portion of the engagement opening is formed at an incline such that the insertion opening portion is located in a vertically higher position than the holding opening portion.

18. The breast pump according to claim 1, further comprising:

a reinforcement rib located on the wall portion.

* * * * *